United States Patent [19]
Farnsworth et al.

[11] 4,078,145
[45] Mar. 7, 1978

[54] PHYTOQUINOID POSSESSING ANTI-TUMOR ACTIVITY

[75] Inventors: Norman R. Farnsworth; Geoffrey A. Cordell; Masaru Ogura, all of Chicago, Ill.

[73] Assignee: University of Illinois Foundation, Urbana, Ill.

[21] Appl. No.: 689,096

[22] Filed: May 24, 1976

[51] Int. Cl.$^2$ .............................................. C07C 69/74
[52] U.S. Cl. .................................. 560/126; 424/305; 424/317
[58] Field of Search .................................. 260/468 K

[56] References Cited
PUBLICATIONS

Siegel et al., Monatsch 84, 910 (1953).
Chem. Abs., 85:130429 (1976).

*Primary Examiner*—Robert Gerstl
*Attorney, Agent, or Firm*—Mathew L. Kalinowski

[57] ABSTRACT

An alcoholic extract of the plant *Jacaranda caucana* (Bignoniaceae) provides in vivo anti-tumor activity against the P-388 lymphocytic leukemia system. Fractionation of the extract by solvent extraction and chromatography afforded the active principle, a novel phytoquinoid derivative named jacaranone.

5 Claims, No Drawings

PHYTOQUINOID POSSESSING ANTI-TUMOR ACTIVITY

BACKGROUND OF THE INVENTION

This invention relates to a novel phytoquinoid derivative possessing anti-tumor activity. More particularly this invention relates to the novel phytoquinoid derivative isolated from the twig-leaf and stem bark parts of the *Jacaranda caucana* Pittier and to a method for isolating it.

Jacaranda species are distributed throughout Central America, northern South America, and the West Indies. Some seventy-four Jacaranda species are known but the genus has been the subject of only limited study. Thus, an aqueous extract of *Jacaranda lasiogyne* has been shown to exhibit anti-tumor activity in the L-1210 system (M. G. Hardinge et al; Cancer Res. 22:981(1963)). Screening of the flora of the Dhawar district indicated that the leaf of *Jacaranda mimosifolia* contained traces of alkaloids (S. P. Hiremath et al; J. Karnatak Univ., 14:49(1969)).

STATEMENT OF THE INVENTION

We have now found that a methanol extract of the twig-leaf and stem bark parts of *Jacaranda caucana* shows a high degree of in vivo anti-tumor activity against the P-388 lymphocytic leukemia system. The methanol extract was further fractionated by dilution with water followed by extraction first with petroleum ether and then with chloroform. This procedure yielded four fractions: a petroleum ether soluble fraction, a chloroform soluble fraction, a chloroform:water insoluble fraction, and a water soluble fraction. Biological evaluation results shown in Table I indicate that most of the activity is in the chloroform soluble fraction from both the stem bark and twig-leaf parts.

TABLE I
BIOLOGICAL DATA AFTER PRELIMINARY FRACTIONATION

| Plant Part | Tumor System | Pet. Ether Soluble | CHCl₃ Soluble | CHCl₃:Aq Insoluble | Aq Soluble |
|---|---|---|---|---|---|
| *J. caucana* stem bark | P-388[a] 9KB[b] | 200/106 100 | 200/134 8.3 | 200/123 8.6 | 200/134 1 |
| *J. caucana* twig-leaf | P-388 9KB | 200/123 100 | 200/163 7.6 | 200/125 2.3 | 200/115 100 |

[a] Dose in mg/kg / T/C
[b] ED₅₀ in μg/ml

Chromatography of the chloroform soluble material from the twig-leaf plant part on silica gel (Florisil) afforded five fractions. Antitumor activity was found to be concentrated in the first two fractions. Further chromatography of each of these two fractions gave a pale yellow oil, to which the name "jacaranone" was given. The oil crystallized slowly on standing, but attempts to recrystallize this material have failed thus far.

The nmr spectrum suggested the presence of a methoxyl group ($\delta 3.740$ ppm) and a deshielded methylene function ($\delta 2.713$ ppm). A broad singlet at $\delta 4.120$ ppm disappeared upon addition of D₂O. The assignment of this absorption to a hydroxy group was substantiated by the infra-red spectrum which showed a strong broad absorption at 3320 cm⁻¹. Two groups of multiplets, each integrating for two protons, centered at $\delta 6.167$ and 6.981 ppm, showed a principal coupling constant of 8.8 Hz. This is a characteristic pattern for a 1,4-substituted aromatic system and could be substantiated by the infrared spectrum which showed a strong absorption at 865 cm⁻¹. From the carbonyl region of the infra-red spectrum the methoxyl group could be traced to an ester function (1745 cm⁻¹). The bands at 1680 and 1635 cm⁻¹ could be assigned to a p-quinoid type system.

The high resolution mass spectrum of jacaranone indicated a molecular formula of $C_9H_{10}O_4$. The oxygen atoms of jacaranone are accounted for by a hydroxy, ester and quinoid functions and the carbon atoms by a six-membered ring, methylene and carbomethoxyl groups.

On this basis, the following structure has been assigned to jacaranone:

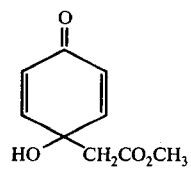

PREFERRED EMBODIMENTS OF THE INVENTION

PLANT MATERIAL — Twig-leaf and stem bark fractions of *Jacaranda caucana* Pittier were collected in Colombia in February 1974. Specimens were air-dried. A herbarium specimen is deposited in the Herbarium of the National Arboretum, Agricultural Research Service, U.S. Department of Agriculture, Washington, D.C.

EXTRACTION PROCEDURE — Approximately one kg each of the milled plant parts were separately extracted by percolation at room temperature with methanol. For large scale work the stem bark (22 kg) and twig-leaf (24 kg) materials were separately extracted in a Soxhlet apparatus with methanol.

PRELIMINARY FRACTIONATION — The methanol solution from the extraction of 1.3 kg of the twig-leaf plant parts of *J. caucana* was evaporated to a thick syrup, water (2 liters) was added, and the mixture extracted with petroleum ether (5 liters). Evaporation of the petroleum ether extract in vacuo gave 15.9 g of residue. The aqueous phase was extracted with chloroform (2 × 1 liter) and the chloroform phase dried (Na₂SO₄), filtered and evaporated in vacuo to give 52.5 g of residue. The aqueous phase was filtered to give a chloroform-aqueous insoluble residue (12 g). The filtered aqueous phase was lyophilized.

The methanol solution from the extraction of 870 g of the stem bark plant parts of *J. caucana* was evaporated to a thick syrup, water (800 ml) was added, and the mixture extracted with petroleum ether (2 liters). Evaporation of the petroleum ether extract in vacuo gave 6.6 g of residue. The aqueous phase was extracted with chloroform (2 × 400 ml) and the chloroform phase dried (Na₂SO₄), filtered and evaporated in vacuo to give 7.64 g of residue. The aqueous phase was filtered to afford a chloroform-aqueous insoluble residue (4.5 g). The filtered aqueous phase was lyophilized.

BIOLOGICAL EVALUATION OF THE PRELIMINARY FRACTIONS — The four preliminary fractions from each plant part were evaluated against the P-388 lymphocytic leukemia system in vivo and the 9KB carcinoma of the nasopharynx in cell culture. These results are summarized in Table I, and as indicated above, the activity was found to be concentrated in the chloroform soluble material.

ISOLATION AND STRUCTURE ELUCIDATION OF JACARANONE — A portion (31.2 g) of the chloroform soluble material from the twig-leaf part of the plant was chromatographed on Florisil (250 g) eluting successively with chloroform (2 × 1 liter), chloroform:methanol (9:1) 2 × 1 liter) and methanol (1 liter). Biological evaluation indicated that the first two fractions contained the active constituent. In vivo activities in the P-388 system were, for the first fraction, T/C 153 at 100 mg/kg, and T/C 142 at 50 mg/kg for the second fraction.

The first fraction (2.5 g) was chromatographed on silica gel (Merck Silica $PF_{254}$) (100 g and eluted in 20 ml fractions successively with benzene (4 liters), benzene:ethyl acetate (20:1) (1 liter), benzene:ethyl acetate (10:1) (3 liters) and methanol (1 liter). Fractions 321-398 from this column were combined and the residue (950 mg) rechromatographed on silica gel (25 g) and eluted with chloroform to afford jacaranone (440 mg). Additional fractions from this column afforded a quantity (150 mg) of crude jacaranone.

From the second fraction (800 mg) by chromatography on silica gel (100 g) a further quantity (725 mg) of crude jacaranone was obtained.

A portion (5 g) of the chloroform soluble material from the stem bark part of the plant was chromatographed on silica gel (25 g) and eluted in 20 ml fractions successively with chloroform (800 ml), chloroform:methanol (100:1) and (400 ml) and methanol (1 liter). From fractions 53-62 of this column pure jacaranone (100 mg) was obtained.

Jacaranone was obtained as a pale yellow oil which crystallized slowly on standing, mp 53°-4° ; uv λ max (EtOH) 225 nm (log ε 4.16); ir ν max (thin film) 3320 (m), 1745 (s), 1680 (vs), 1635 (s), 1450 (m), 1185 (m), 1170 (m), 1075 (m), 1040 (m), 1005 (m) and 865 (s) cm$^{-1}$; nmr ($CDCl_3$, 60MHz) δ 2.713 (2H,s), 3.740 (3H,s), 4.120 (1H,bs, removed with $D_2O$), 6.167 (2H,m) and 6.981 (2H,m); cmr ($CDCl_3$, 25.1 MHz) (proton-noise decoupled) δ 43.4 (C-7), 52.3 (C-9), 67.3 (C-4), 128.2 (C-2,6), 149.0 (C-3,5), 171.0 (C-8) and 185.0 (C-1); ms M$^+$ m/e 182 (13%) 150 (20), 122 (15), 109 (100), 81 (30) and 74 mu (94). The high resolution mass spectrum showed M$^+$ m/e 182.05892, (calcd. for $C_9H_{10}O_4$, 182.05791).

Although the present invention has been described with reference to certain specific preferred embodiments thereof, the invention is not limited thereto, but includes within its scope such modifications and variations as come within the scope and spirit of the appended claims.

We claim:

1. The lower aliphatic alcohol extract from the plant *Jacaranda caucana* Pittier containing jacaranone in amounts sufficient to show *in vivo* anti-tumor activity in the lymphocytic leukemia P 388 system.

2. A method of preparing the extract of claim 1 comprising the steps of extracting the twig-leaf or stem bark parts of *Jacaranda caucana* Pittier with a lower aliphatic alcohol followed by removing a portion or all of the alcohol.

3. The method of claim 2 wherein the lower aliphatic alcohol is methanol.

4. The method of claim 3 including the additional steps of diluting the concentrated methanol mixture with water, extracting the aqueous mixture first with petroleum ether then with chloroform, and isolating a residue from the chloroform extract having *in vivo* anti-tumor activity in the lymphocytic leukemia P 388 system.

5. The method of claim 4 including the step of purifying the residue by chromatographing a chloroform solution of the residue on silica gel followed by eluting the purified residue with chloroform.

* * * * *

UNITED STATES PATENT AND TRADEMARK OFFICE
CERTIFICATE OF CORRECTION

PATENT NO. : 4,078,145
DATED : March 7, 1978
INVENTOR(S) : Norman R. Farnsworth et al.

It is certified that error appears in the above-identified patent and that said Letters Patent are hereby corrected as shown below:

Column 1, after line 4 insert:  -- The invention described herein was made in the course of work under a contract from the Department of Health, Education and Welfare. --

Signed and Sealed this

Tenth Day of July 1979

[SEAL]

Attest:

Attesting Officer

LUTRELLE F. PARKER
Acting Commissioner of Patents and Trademarks